// 
US006272365B1

(12) United States Patent
Ronkainen et al.

(10) Patent No.: US 6,272,365 B1
(45) Date of Patent: Aug. 7, 2001

(54) CONNECTING ARRANGEMENT AT HEART RATE MONITOR AND ELECTRODE BELT

(75) Inventors: Ilkka Ronkainen, Oulu; Jarmo Lehtonen, Turku, both of (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 09/336,945

(22) Filed: Jun. 21, 1999

(30) Foreign Application Priority Data

Jun. 22, 1998 (FI) .......................................... 981436
Apr. 1, 1999 (FI) ................................... 990158 U

(51) Int. Cl.[7] .................................................. A61B 5/0408
(52) U.S. Cl. ......................... 600/390; 600/393; 607/149
(58) Field of Search ................................. 600/382–386, 600/388, 390, 393; 607/145, 152

(56) References Cited

U.S. PATENT DOCUMENTS

| 4,122,843 | 10/1978 | Zdrojkowski . | |
|---|---|---|---|
| 4,275,743 | * 6/1981 | Hjort . | |
| 4,502,192 | 3/1985 | Hess . | |
| 4,709,702 | 12/1987 | Sherwin . | |
| 5,140,992 | 8/1992 | Zuckerwar et al. . | |
| 5,464,021 | * 11/1995 | Birnbaum | 600/390 |
| 5,491,474 | * 2/1996 | Suni | 128/903 |
| 5,657,514 | 8/1997 | Fabrizio . | |

FOREIGN PATENT DOCUMENTS

| 26 10 337 | 9/1977 | (DE) . | |
|---|---|---|---|
| 2831412 | * 1/1980 | (DE) | 600/390 |
| 418218 | 10/1934 | (GB) . | |
| 494367 | 10/1938 | (GB) . | |

* cited by examiner

*Primary Examiner*—Lee Cohen
(74) *Attorney, Agent, or Firm*—Hoffman & Baron, LLP

(57) ABSTRACT

The invention relates to a connecting arrangement between an electrode belt and a circumferential band at a heart rate monitor, the arrangement comprising the electrode belt for measuring heartbeat at a person's chest, which electrode belt comprises one or more electrodes and one or more sockets, provided with an opening and one or more supporting structures, the connecting arrangement further comprising the circumferential band provided with one or more connecting heads for keeping the electrode belt on the person's chest, the electrode belt and the circumferential band being connectable to each other by using one or more connections of the connecting arrangement, which connection can be provided by placing a connecting head in a socket. In the connecting arrangement, said one or more supporting structures of said one or more sockets are directed to the same side as said one or more electrodes, whereby the connecting head can be passed from the side of the electrode belt opposite to the side comprising an electrode to the side comprising an electrode, for placing the connecting head in the socket.

11 Claims, 5 Drawing Sheets

CONNECTING ARRANGEMENT AT HEART RATE MONITOR AND ELECTRODE BELT

BACKGROUND OF THE INVENTION

1. Field of the Invention

The invention relates to a connection between an electrode belt belonging to a heart rate monitor and to be positioned on the chest and a circumferential band to be wound around the body and to the structure of the electrode belt, as far as the above connection is concerned. A heart rate monitor is a device used in sports and medicine, the device measuring the pulse of a human heart by means of an electrode belt on the chest or by means of a device based on pressure measurement at the wrist.

2. Brief Description of the Related Art

Heart rate monitors typically comprise an electrode belt, a circumferential band and a display unit at the wrist. At its ends, the electrode belt is fastened to the circumferential band that is wound around the body of the person to be measured. Inside the electrode belt, on the side to be positioned against the body, there are electrodes measuring the electrical pulses generated by heartbeat, which pulses are then sent by a sender of the electrode belt to a receiver for instance at the wrist, the receiver also containing a memory and a display unit. Moreover, heart rate monitors can have such a structure that the electrode belt on the chest also comprises functions, such as display and memory, which were included in the receiver at the wrist in the above solution. Naturally, a heart rate monitor like this needs no transmitter-receiver technique, because all functions are contained in the electrode belt to be positioned on the chest. Some heart rate monitors have a structure comprising measuring devices at the wrist only, which measure the heartbeat by means of pressure changes in arteries. The present invention relates to heart rate monitors, comprising an electrode belt to be kept on the chest, and the invention relates especially to a connection between the electrode belt and a circumferential band and to the structure of the electrode belt, as far as the connection is concerned.

In accordance with the prior art, the connection between the electrode belt and the circumferential band consists in that a lock button of the band is passed from the inside (the side against the body) of the electrode belt through a hole in a mounting socket of the electrode belt and placed in the mounting socket outside the electrode belt. With the lock button mounted in the socket, the plane surfaces of the socket keep the button in place so that the button is not capable of returning inside the electrode belt, in which case the connection between the electrode belt and the circumferential band would come loose.

However, a drawback is associated with the prior art technique: when the electrode belt and the circumferential band are placed against the body and when the circumferential band is tightened in such a way that the electrode belt stays on the chest, the connection point is subjected to a force caused by the bent electrode belt and the tightened circumferential band, which force tries to drive the lock button out of the mounting socket. When the electrode belt has been placed on the chest, a force to the left of the person in question has an anticlockwise effect and a force to the right of the person has a clockwise effect. The problem becomes critical as for children and slim adults having a narrow chest: the electrode belt must then be bent much and the force directed to the connection between the electrode belt and the circumferential band is stronger still than when people with a broad chest are concerned.

SUMMARY OF THE INVENTION

The aim of the present invention is to provide a connecting arrangement of new type, which avoids the problems associated with the known solutions. This aim is achieved by means of a solution according to the invention, the object of which is a connecting arrangement between an electrode belt and a circumferential band at a heart rate monitor, the arrangement comprising the electrode belt for measuring heartbeat at a person's chest, which electrode belt comprises one or more electrodes and one or more sockets provided with a hole and one or more supporting structures, the connecting arrangement further comprising the circumferential band provided with one or more connecting heads for keeping the electrode belt on the person's chest, the electrode belt and the circumferential band being connectable to each other by using one or more connections of the connecting arrangement, which connection can be provided by placing a connecting head in a socket. The invention is characterized in that said one or more supporting structures of said one or more sockets are directed to the same side as said one or more electrodes, whereby the connecting head can be passed from the side of the electrode belt opposite to the side comprising an electrode to the side comprising an electrode, for placing the connecting head in the socket.

Another object of the invention is an electrode belt of a heart rate monitor for measuring heartbeat at a person's chest, the electrode belt comprising one or more electrodes for detecting the heartbeat and one or more sockets provided with one or more supporting structures for one or more connecting heads of a circumferential band for fastening the electrode belt. The invention is characterized in that said one or more supporting structures of said one or more sockets are directed to the same side of the electrode belt as said one or more electrodes.

Preferred embodiments of the invention constitute the object of independent claims.

The connecting arrangement and the electrode belt of the invention provide that significant advantage that, when the electrode belt and the circumferential band are fastened to each other, placed around the body and tightened, and the electrode belt is curving, the connecting head of the circumferential band tends to be positioned in the mounting socket stronger and stronger, while the locking head is pressed against the plane surfaces. By means of the invention, the force caused by the curving electrode belt can be utilized to provide a better connection. This is true for slim adults and children, in particular, whereby the force caused by the curvature of the belt to the connection leads to that the connecting head is pressed stronger and stronger into the socket to provide a better connection.

BRIEF DESCRIPTION OF THE FIGURES

In the following, the invention will be described in more detail with reference to the enclosed drawings, in which.

DETAILED DESCRIPTION OF THE INVENTION

Figure 1:
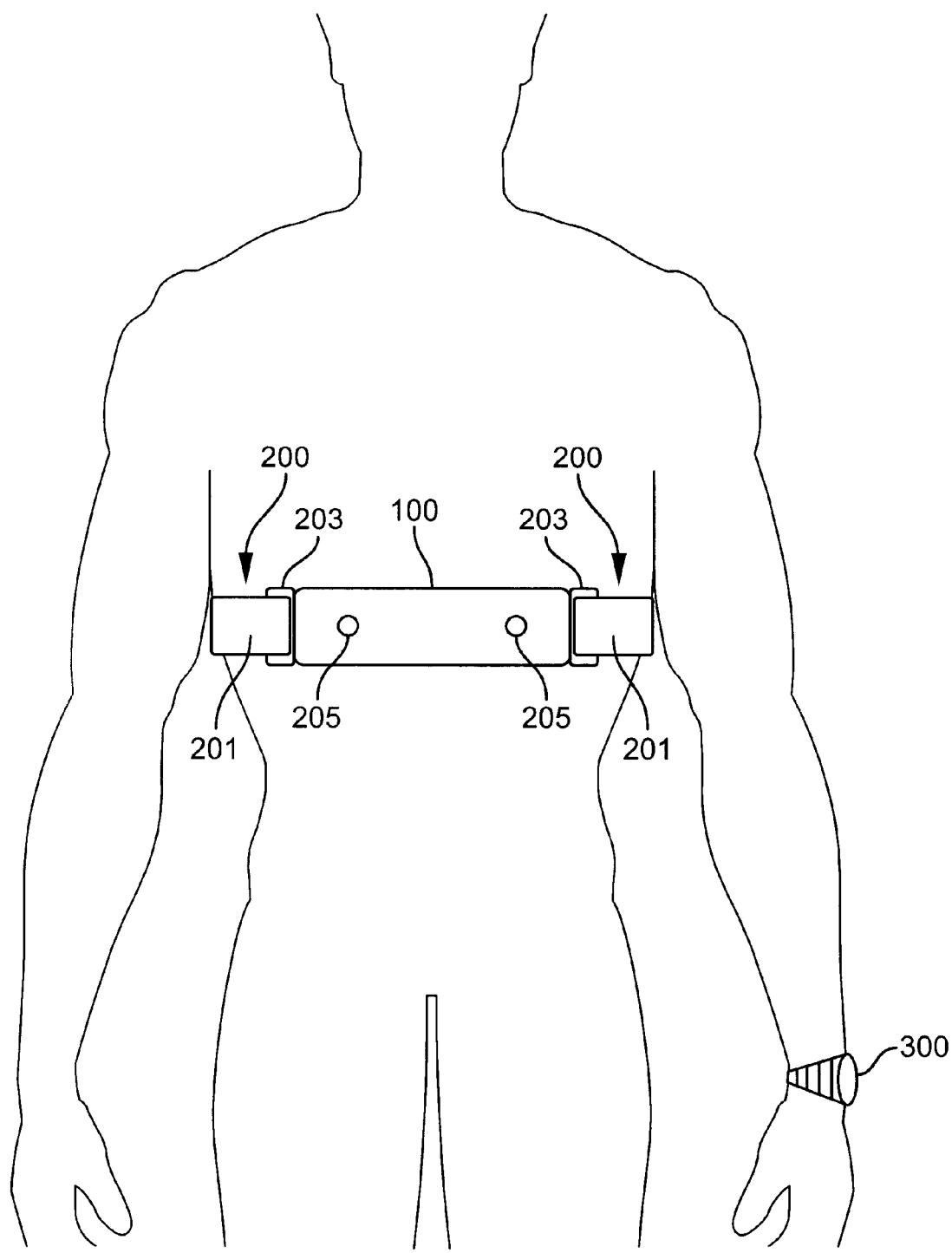
FIG. 1 shows an electrode belt placed on a person's chest and a circumferential band, the connection between them and the structure of the electrode belt belonging to the prior art technique.

A connection according to the invention will be described in the following by means of FIGS. 1 to 5B. Initially, according to FIG. 3A, an electrode belt 100 comprises an inside 110 and at least one electrode 111 and, according to FIG. 3B, an electrode belt 100 comprises an outside 130. Referring to FIG. 3A again, the electrode belt comprises a socket 112 provided with supporting structures 113. According to FIG. 5B, a socket comprises an edge 112a and, according to FIG. 3B, the electrode belt comprises an opening 114 and a recess 131.

Figure 4A:
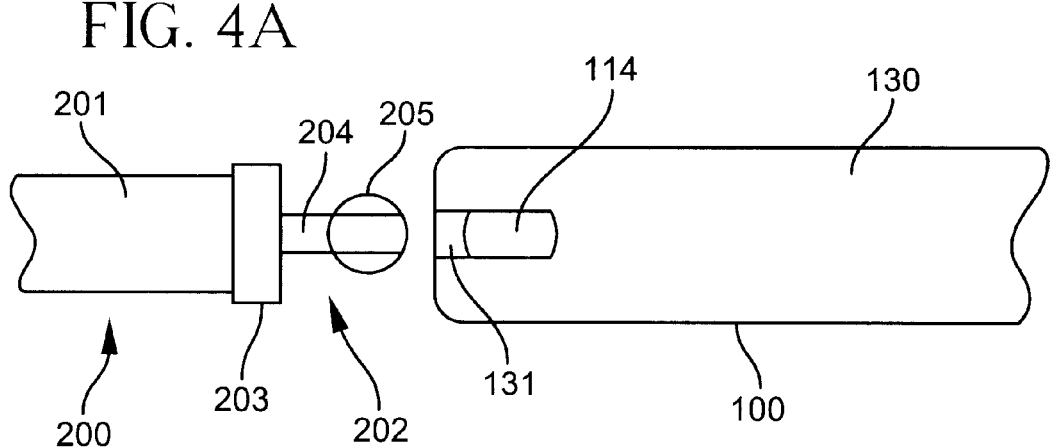
FIG. 4A shows the electrode belt from outside and the circumferential band before connection.

Further, referring to FIG. 4A, a circumferential band 200 comprises a band 201 and a buckle 202, the buckle 202 comprising a band connection 203, a connecting arm 204 and a connecting head 205.

In the following, a preferred embodiment of the invention is described with reference to the FIGS. 1 to 5B. Initially, reference is made to FIG. 1, showing a prior art electrode belt 100 placed on a person's chest and at its both ends fastened to a circumferential band 200 wound around the body. In the Figure, the electrode belt 100 on the chest measures heartbeat and sends pulse information to a receiver 300 at the wrist, the receiver also serving as a user interface at the use of a heart rate monitor and as a display unit. Alternatively, heart rate monitors have been implemented in such a way that an electrode belt on the chest attends, besides to pulse measurement, also to storing, processing and display of pulse information, which makes a separate device at the wrist unnecessary. In FIG. 1, the connections between the electrode belt 100 and the circumferential band 200 in accordance with the prior art are made in such a way that the connecting heads 205 of the circumferential band 200 are passed through the electrode belt from inside, i.e. from the side to be placed against the body. As appears from the figure, the connecting heads 205 are positioned at the electrode belt 100 in such a way that they can be seen on the outside of the electrode belt, and the connecting arms of the buckles 203 are situated on the inside of the electrode belt and cannot be seen from the outside. Now, upon positioning the electrode belt of the figure in place for use and upon tightening it by the circumferential band 200 to a suitable tightness, a force caused by the curving electrode belt is directed perpendicularly away from the body to the connection between the circumferential band and the electrode belt. The force extending away from the body tends to press the electrode belt away from the body, and because the connecting heads 205 of the circumferential band are placed in the sockets of the electrode belt 100, said force is directed through the plane surfaces of the sockets to the connecting heads and tries to drive them out of their sockets. The problem is accentuated with slim adults and children, having a narrow chest. Then, when the electrode belt has been positioned in place, the connecting heads are situated at the edges of the body at points where the curvature of the body is considerable. The connecting heads are thereby subjected to an especially strong force, driving them out of the sockets.

Figure 2:
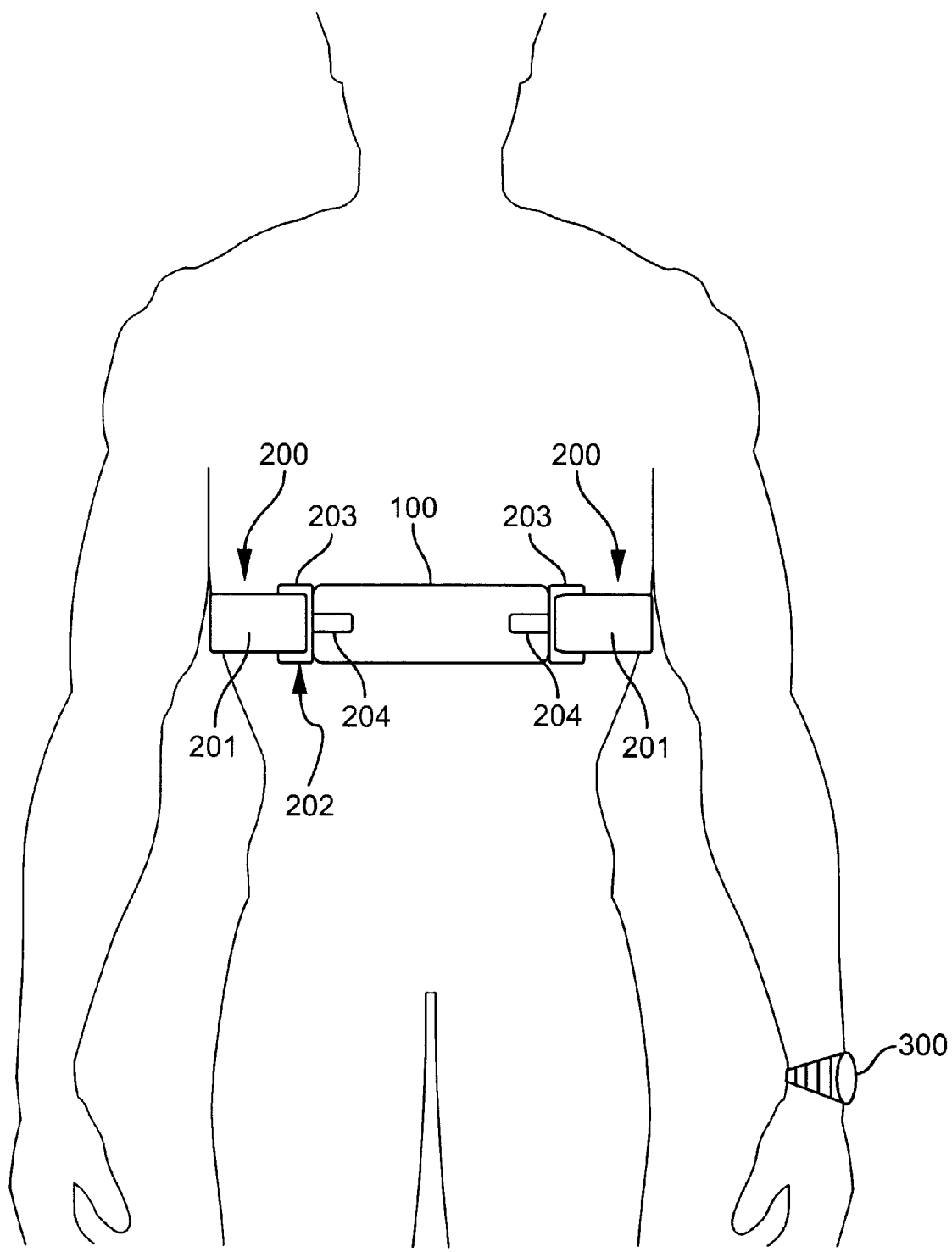
FIG. 2 shows an electrode belt placed on a person's chest and a circumferential band, the connection between them and the structure of the electrode belt agreeing with the inventions.

FIG. 2 shows, in the same way as FIG. 1, an electrode belt 100 placed on a person's chest, but now using a connection of the invention between the electrode belt and a circumferential band 200. In a preferred embodiment of the invention, the electrode belt comprises two sockets and the circumferential band two connecting heads, respectively. A connection between the electrode belt and the circumferential band can still be implemented by one connection according to the invention, whereby the other ends of the electrode belt and the circumferential band are detachably connectable by means of another connecting solution or they are fixedly connected together. In a preferred embodiment of the solution of the invention, the connecting heads are substantially circular button-like pieces, but they can also be quadratic or rectangular.

Further, referring to FIG. 2, the band 201 of the circumferential band 200 is preferably made of elastic cloth, the both ends of the band being preferably provided with buckles 202 by sewing a loop at the band, for instance, to which loop a band fastener 203 of the buckle can be fastened. According to the solutions of the prior art, the band can be tightened around a person to a suitable tightness. The buckles are preferably made of plastic or metal. A connecting arm with a connecting head fastened thereto is also attached to the band fasteners of the buckles, to which fasteners the band can be fastened. In the solution of the invention, with the electrode belt 100 of FIG. 2 positioned in place for use and tightened by means of the circumferential band 200 to a suitable tightness, a force directed from the body outwards tries to press the connecting heads into the sockets of the electrode belt stronger and stronger. Reference is made to FIG. 1, where a force directed from the body outwards had a detrimental effect because it drove the connecting heads out of the sockets. In the solution of FIG. 2, the force directed from the body outwards and caused by the curvature of the electrode belt acts to the benefit of the connection by making the connecting heads press against the plane surfaces of the socket. In the case of slim adults and children, with the electrode belt positioned in place and the connecting heads located at strongly curved points at the edges of the body, the strong force directed to the connecting heads acts for these people, because the electrode belt stays in place well, thanks to forces caused by the circumferential band and the electrode belt curving along the body.

Figure 3A:
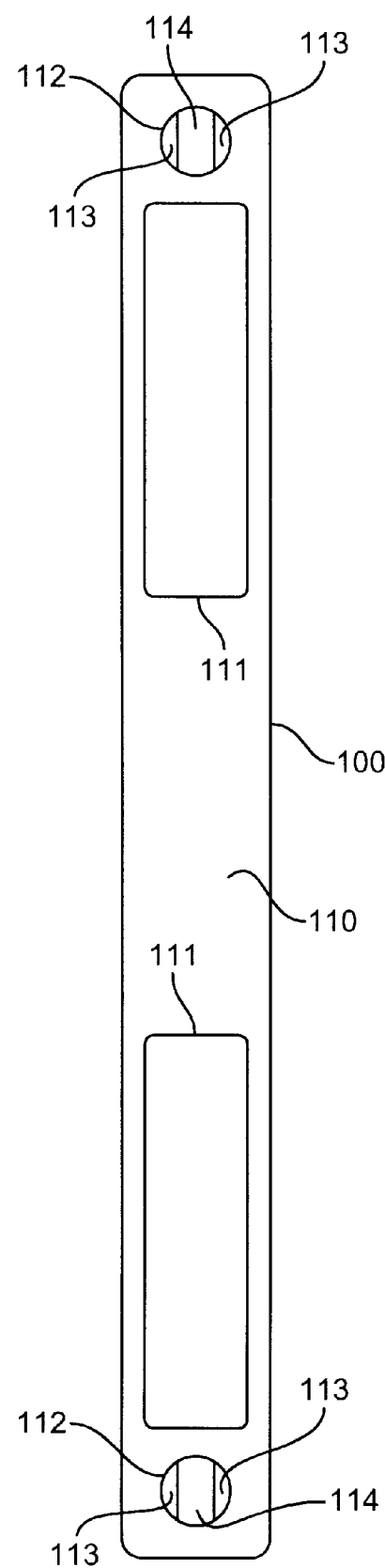
FIG. 3A shows that side of the electrode belt of the invention which is to be placed against the body of the person to be measured.
Figure 3B:
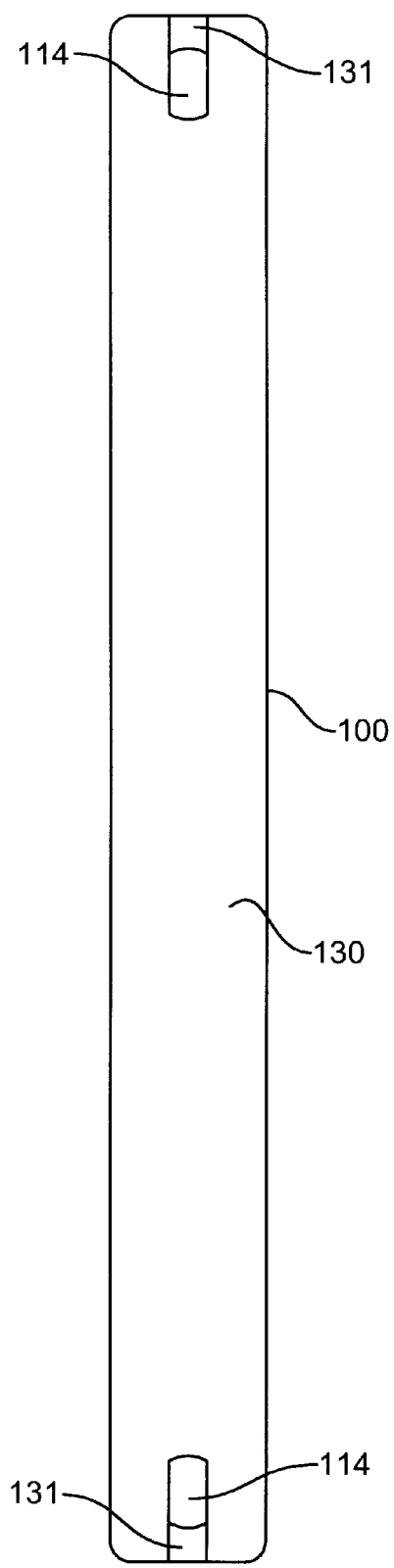
FIG. 3B shows the electrode belt of the invention from outside, i.e. from the side opposite to that to be placed against the body of the person to be measured.

FIG. 3A shows the inside 110 of an electrode belt 100, i.e. the side provided with electrodes 111 and to be placed against the body, and FIG. 3B shows the outside 130 of the same electrode belt. From FIG. 3A appears that the supporting structures 113 of sockets 112, the structures preferably being semi-circular plane surfaces, are visible when the electrode belt is looked at from inside. In addition, the sockets 112 comprise openings 114 according to FIGS. 3A and 3B; through an opening, a connecting head can be passed in such a way that it is brought from the outside to the inside and placed in the socket.

Figure 4B:
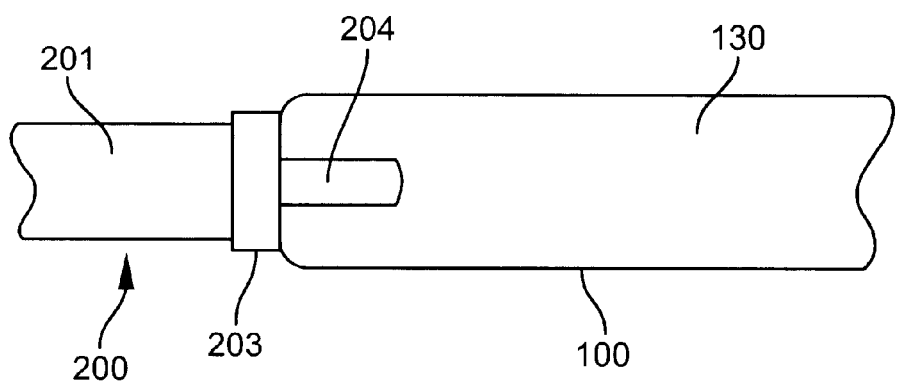
FIG. 4B shows the electrode belt from outside and the circumferential band after a connection has been made.
Figure 4C:
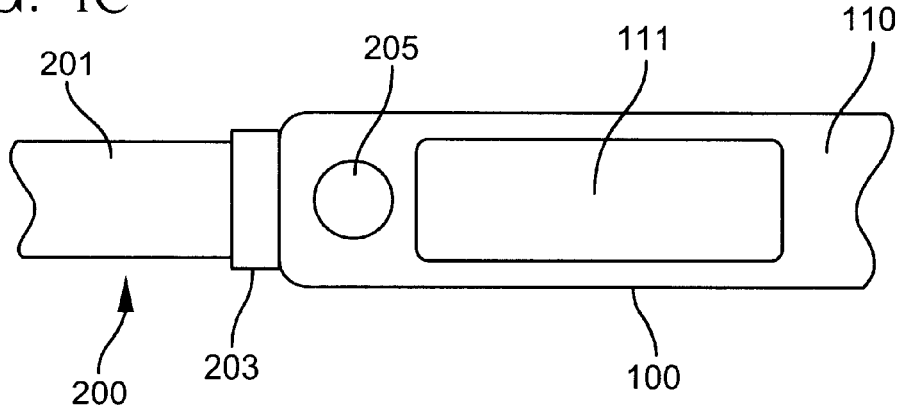
FIG. 4C shows the electrode belt from inside and the circumferential band after a connection has been made.

FIGS. 4A to 4C show how a connection is made by placing a connecting head 205 in a socket 112. In FIGS. 4A and 4B, an electrode belt 100 is shown from the outside 130 and in FIG. 4C from the inside 110. From FIG. 4A appears that, when a connecting head is passed from the outside of the electrode belt, the connecting head 205 is located behind a connecting arm 204. For the connecting head 205 to be passed through an opening 114, it is turned laterally about 90 degrees. From FIG. 4B appears that, after a connecting head 205 has been placed in a socket 112, a connecting arm 204 fills a recess 131 in the electrode belt 100, the depth of the recess corresponding to the thickness of the connecting arm, whereby the connecting arm is positioned essentially at the same level as the rest of the electrode belt. The fact that the connecting arm fills the recess and the opening is advantageous for the use, because the opening and the recess support the connecting arm and prevent its lateral movement when the connection has been completed. From FIG. 4C is seen that, with a button in place, only a connecting head 205 of the connection is visible on the inside 110. This figure can be compared to the FIG. 1 according to the prior art, taken from the outside and being similar to FIG. 4C. The figure shows further that the connecting head, having an area preferably substantially equal to that of a socket, fills the socket.

Figure 5A:
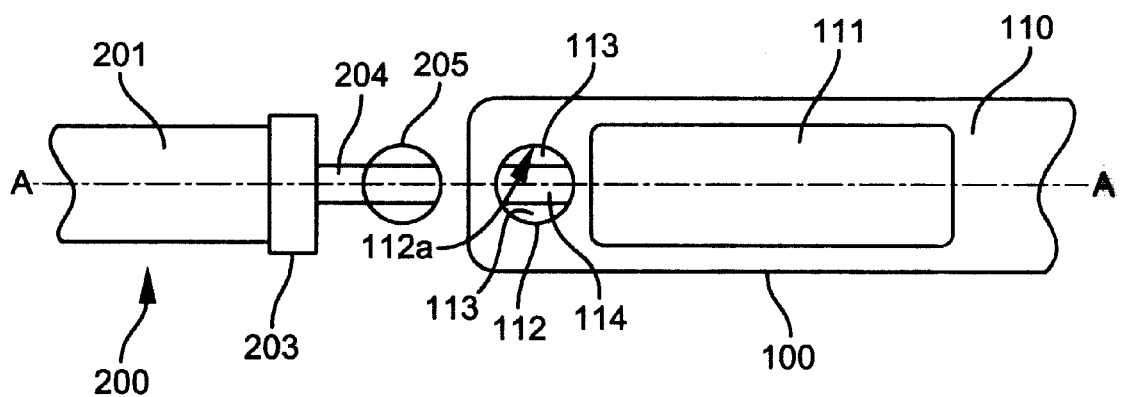
FIG. 5A shows the electrode belt from inside and the circumferential band before connection.
Figure 5B:
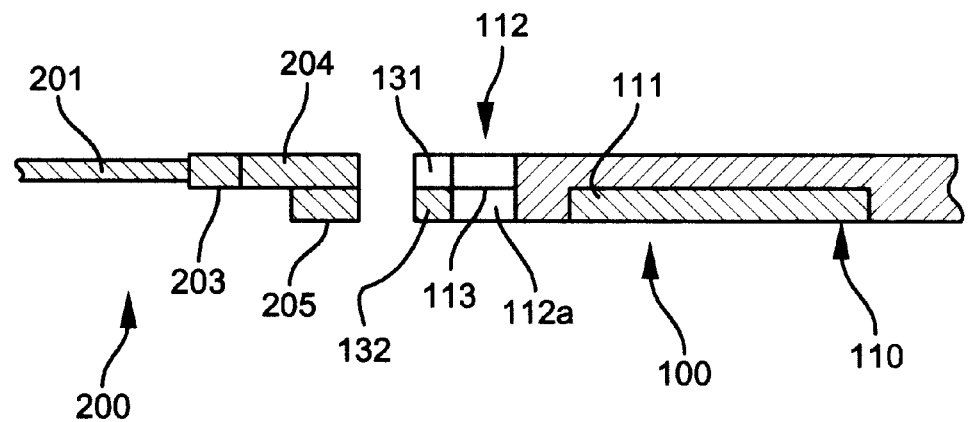
FIG. 5B shows a general side view of the flexible band and the electrode belt and, as to the socket, a section of the situation of FIG. 5A.

FIG. 5A illustrates the inside 110 of an electrode belt 100 before a connecting head 205 is passed into a socket 112, and from the figure appears that, when the situation is examined from the inside, the connecting head is located in front of a connecting arm 204. FIG. 5B shows a figure, corresponding to FIG. 5A, along a section A—A, when both a circumferential band and an electrode belt have been turned 90 degrees, the side profiles of these parts being illustrated in such a way that the side to be placed against the body is down in the figure. In FIG. 5B, a connecting head 205 and a connecting arm 204 are substantially equally thick in one preferred embodiment, and likewise, a recess 131 of the connecting arm in the electrode belt 100 and the connecting arm 204 are mutually substantially equally thick. Seen from the inside 110 of the electrode belt 100, sockets have an insertion 132 which also has a thickness substantially equal to that of the connecting head 205. When the circumferential band and the electrode belt of the figure are connected together, those sides of the connecting head 205 which face the connecting arm 204 are placed against the supporting structures 113 and the edges of the connecting head are placed against the edges 112a of the socket 112. When so connected and the electrode belt 100 is placed against the chest, the connecting head 205 is located substantially against the chest.

Even though the invention is described above with reference to the examples of the attached drawings, it is obvious that the invention is not restricted to them, but it can be modified in many ways within the scope of the inventive idea of the attached claim.

What is claimed is:

1. A connecting arrangement between an electrode belt and a circumferential band, the arrangement comprising the electrode belt for measuring heartbeat at a person's chest, which electrode belt comprises one or more electrodes and one or more sockets, each socket provided with an opening and one or more supporting structures, the connecting arrangement further comprising the circumferential band provided with one or more connecting heads for keeping the electrode belt on the person's chest, the electrode belt and the circumferential band being connectable to each other by placing a connecting head through the opening and in a socket, wherein said one or more supporting structures of said one or more sockets are directed to the same side as said one or more electrodes, whereby the connecting head can be passed through the opening and positioned in a socket from the side of the electrode belt opposite to the side comprising an electrode to the side comprising an electrode, for placing the connection head in the socket and wherein, when such a connection is closed and the electrode belt is placed against the chest, the connecting head is located substantially against the chest.

2. A connecting arrangement according to claim 1, wherein the circumferential band comprises a connecting arm, by means of which the connecting head and the circumferential band are in contact with each other.

3. A connecting arrangement according to claim 2, wherein the electrode belt comprises one or more recesses on the side of the electrode belt opposite to the side comprising electrodes, in which recess the connecting arm can be inserted when a connection is made.

4. A connecting arrangement according to claim 1, wherein the supporting structures of the socket are two substantially semi-circular plane surfaces.

5. A connecting arrangement according to claim 1, wherein the supporting structures of the socket are embedded in the electrode belt from the side of the electrode belt comprising electrodes.

6. A connecting arrangement according to claim 1, wherein the area of the connecting head is substantially equal to the total area of the supporting structures of the socket and the opening.

7. A connecting arrangement according to claim 1, wherein the connecting head is a substantially circular button.

8. An electrode belt of a heart rate monitor for measuring heartbeat at a person's chest, the electrode belt comprising one or more electrodes for detecting the heartbeat and one or more sockets provided with one or more supporting structures for one or more connecting heads of a circumferential band for fastening the electrode belt, wherein said one or more supporting structures of said one or more sockets are directed to the same side of the electrode belt as said one or more electrodes and wherein the socket of the electrode belt comprises an opening through which the connecting head of the circumferential band can be passed from the side of the electrode belt opposite to the side comprising the electrodes for placing the connecting head in the socket.

9. An electrode belt according to claim 8, wherein the electrode belt comprises one or more recesses on the side of the electrode belt opposite to the side comprising electrodes, into which recesses a connecting arm of the circumferential band can be inserted when a connection is made.

10. An electrode belt according to claim 8, wherein the supporting structures of the socket are two substantially semi-circular plane surfaces.

11. An electrode belt according to claim 8, wherein the supporting structures of the socket are embedded from the side of the electrode belt comprising the electrodes.

* * * * *